US010287320B2

(12) United States Patent
Svendsen et al.

(10) Patent No.: US 10,287,320 B2
(45) Date of Patent: May 14, 2019

(54) ANTI-LYMPHOMA PEPTIDES

(71) Applicant: Universitetet i Tromsø—Norges Arktiske Universitet, Tromsø (NO)

(72) Inventors: John Sigurd Svendsen, Kvaløysletta (NO); Øystein Rekdal, Billingstad (NO); Johannes Eksteen, Tromsø (NO)

(73) Assignee: Universitetet i Tromsø—Norges Arktiske Universit (NO)

( * ) Notice: Subject to any disclaimer, the term of this patent is extended or adjusted under 35 U.S.C. 154(b) by 164 days.

(21) Appl. No.: 15/116,148

(22) PCT Filed: Feb. 4, 2015

(86) PCT No.: PCT/EP2015/052333
§ 371 (c)(1),
(2) Date: Aug. 2, 2016

(87) PCT Pub. No.: WO2015/118028
PCT Pub. Date: Aug. 13, 2015

(65) Prior Publication Data
US 2017/0073372 A1    Mar. 16, 2017

(30) Foreign Application Priority Data

Feb. 4, 2014  (GB) .................................. 1401877.4

(51) Int. Cl.
*C07K 7/08* (2006.01)
*C07K 7/06* (2006.01)
(Continued)

(52) U.S. Cl.
CPC .................. *C07K 7/08* (2013.01); *C07K 7/06* (2013.01); *A61K 38/00* (2013.01); *A61K 38/03* (2013.01)

(58) Field of Classification Search
CPC .......... A61K 38/00; A61K 38/03; C07K 7/06; C07K 7/08
See application file for complete search history.

(56) References Cited

U.S. PATENT DOCUMENTS 6,495,663 B1 * 12/2002 Rothbard ............. A61K 31/785
530/329
2003/0166571 A1    9/2003 Judd
(Continued)

FOREIGN PATENT DOCUMENTS

CA         2938705       8/2016
CN      103044522 A      4/2013
(Continued)

OTHER PUBLICATIONS

Alhakamy et al., Polyarginine Molecular Weight Determines Transfection Efficiency of Calcium Condensed Complexes, Mol. Pharmaceutics, vol. 10:1940-1948 (Mar. 27, 2013) (Year: 2013).*
(Continued)

*Primary Examiner* — Randall L Beane
(74) *Attorney, Agent, or Firm* — Ballard Spahr LLP

(57) ABSTRACT

The present invention provides a peptide which: (i) consists of 10 to 16 amino acids; (ii) has at least 8 cationic amino acids with either (a) a side chain comprising a guanidinium group, or (b) a side chain comprising an amino group, of which no more than 7 are consecutive; and (iii) has 2 or 3 tryptophan residues which are not both, or not all, consecutive, said peptide optionally in the form of a salt, ester or amide, or a peptidomimetic of said peptide. The invention further relates to pharmaceutical compositions containing these compounds, the use of these compounds in therapy, particularly as anti-tumor (e.g. anti-lymphoma) agents and non-therapeutic uses of these compounds.

Figure 1:
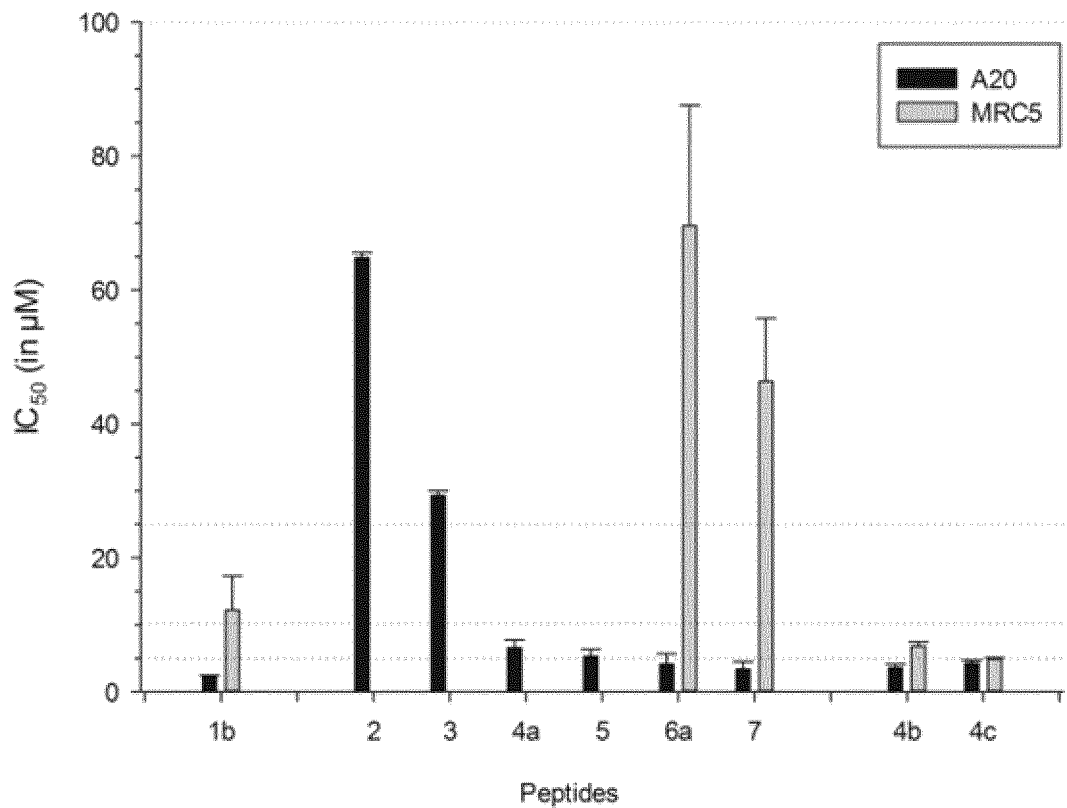

7 Claims, 7 Drawing Sheets
Specification includes a Sequence Listing.

(51) Int. Cl.
A61K 38/03 (2006.01)
A61K 38/00 (2006.01)

(56) References Cited

U.S. PATENT DOCUMENTS

| | | | |
|---|---|---|---|
| 2003/0203415 | A1 | 10/2003 | Rondon et al. |
| 2004/0019181 | A1 | 1/2004 | Falla et al. |
| 2008/0019993 | A1 | 1/2008 | Eliassen et al. |
| 2008/0255052 | A1 | 10/2008 | Selsted et al. |
| 2009/0099533 | A1 | 4/2009 | Montelaro et al. |
| 2010/0112089 | A1 | 5/2010 | Kawabe et al. |
| 2011/0318364 | A1* | 12/2011 | Haug .............. A61K 38/08 424/159.1 |

FOREIGN PATENT DOCUMENTS

| | | | | |
|---|---|---|---|---|
| EP | | 15703272 | 8/2016 | |
| EP | | 3102229 A1 | 12/2016 | |
| JP | | 2002-523517 A | 7/2002 | |
| JP | | 2005247721 A | 9/2005 | |
| JP | | 2016550750 | 8/2016 | |
| WO | WO-00/012541 | A2 | 3/2000 | |
| WO | WO-00/59939 | A1 | 10/2000 | |
| WO | WO-01/19852 | A2 | 3/2001 | |
| WO | WO-2004/094462 | A2 | 11/2004 | |
| WO | WO-2005082399 | A2 * | 9/2005 | ......... A61K 38/1709 |
| WO | WO-2007107748 | A2 * | 9/2007 | ............ A61K 38/16 |
| WO | WO-2009/010540 | A1 | 1/2009 | |
| WO | WO-2010/060497 | A1 | 6/2010 | |
| WO | WO-2012101156 | A2 * | 8/2012 | ............ C07K 14/79 |
| WO | WO-2012/154959 | A1 | 11/2012 | |
| WO | PCT/EP2015/052333 | | 2/2015 | |
| WO | WO-2015/118028 | A1 | 8/2015 | |

OTHER PUBLICATIONS

GenBank: BAJ14339.1, rev protein, partial [Simian immunodeficiency virus] (first submitted Apr. 6, 2010), available at https://www.ncbi.nlm.nih.gov/protein/BAJ14339.1 (last visited Jul. 26, 2018) (Year: 2010).*

Klase et al., A peptide-loaded dendritic cell based cytotoxic T-lymphocyte (CTL) vaccination strategy using peptides that span SIV Tat, Rev, and Env overlapping reading frames, Retrovirology, vol. 3(1), doi:10.1186/1742-4690-3-1, 13 pages (Jan. 6, 2006) (Year: 2006).*

Park et al., Cell specificity, anti-inflammatory activity, and plausible bactericidal mechanism of designed Trp-rich model antimicrobial peptides, Biochimica et Biophysica Acta 1788 (2009) 1193-1203 (Year: 2009).*

He et al.(Novel Synthetic Antimicrobial Peptides against *Streptococcus mutans* , Antimicrobial Agents and Chemotherapy, Apr. 2007 , p. 1351-1358 (Year: 2007).*

Smirnova et al., Russian Journal of Bioorganic Chemistry, vol. 30, No. 5, 2004, pp. 409-416 (Year: 2004).*

International Search Report and Written Opinion dated May 4, 2015 for application PCT/EP2015/052333, filed on Feb. 4, 2015 and published as WO 2015/118028 on Aug. 12, 2015 (Applicant—Universitetet i Tromsø—Norges Arktiske Universitet // Inventor—John S. Svendsen, et al.) (13 pages).

International Preliminary Report on Patentability was dated Aug. 9, 2016 by the International Searching Authority for Application No. PCT/EP2015/052333 dated Feb. 4, 2015 and published as WO 2015/118028 on Aug. 13, 2015(Applicant—Universitetet i Tromsø—Norges Arktiske Universitet; Inventor—John Sigurd Svendsen et al) (8 pages).

Albada, H. B., "Modulating the activity of short arginine-tryptophan containing antibacterial peptides with N-terminal metallocenoyl groups", Belstein Journal of Organic Chemistry, 8: 1753-1764 (2012).

Berge G. et al., "Therapeutic vaccination against a murine lymphoma by intratumoral injection of a cationic anticancer peptide", Cancer Immunol Immunother, 59: 1285-1294 (2010).

Chan, D. I. et al.,"Tryptophan and arginine-rich antimicrobial peptides: structures and mechanisms of action", Biochimica et Biophysica Acta 1758: 1184-1202 (2006).

Deslouches, B. et al.,"Rational design of engineered cationic antimicrobial peptides consisting exclusively of arginine and tryptophan and their activity against multi-drug resistant pathogens", Antimicrobial Agents and Chemotherapy 57(6): 2511 (2013).

Lim, K. et al., "Immobilization studies of an engineered arginine-tryptophan-rich peptide on a silicone surface with antimicrobial and antibiofilm activity", ACS Applied Materials and Interfaces, 5: 6412-6422 (2013).

Rydberg, H. A. et al., "Effect of tryptophan content and backbone spacing on the uptake efficiency of cell penetrating peptides" Biochemistry 51: 5531-5539 (2012).

Shin E. H. et al.,"Trp-Arg-Trp-Trp-Trp-Trp antagonize formyl peptide receptor like 2-mediated signalling", Biochemical and Biophysical Research Communications 341: 1317-1322 (2006).

Shirazi, A. N., et al.,"Cyclic peptides containing tryptophan and arginine as SRC kinase inhibitors", Bioorg Med Chem Lett, 23 (11): 3230-3234 (2013).

Tørfoss et al., "Synthesis of anticancer heptapeptides containing a unique lipophilic $\beta^{2,2}$-amino acid building block", Journal of Peptide Science, 18(3): 170-6 (2012).

Vogel, H. J., et al. "Towards a structure function analysis of bovine lactoferrin and related tryptophan and arginine-containing peptides", Biochem. Cell Biol. 88: 49-63 (2002).

Walrant, A. et al., "Different membrane behaviour and cellular uptake of three basic arginine-rich peptides", Biochimica et Biophysica Acta 1808: 382-393 (2011).

Yang, S. T., et al., "Different modes in antibiotic action of triptrpticin analogs, cathelicidin-derived Trp-rich and Pro/Arg-rich peptides", Biochimica et Biophysica Acta 1758: 1580-1586 (2006).

Yeaman, M. R. et al, "Mechanisms of antimicrobial peptide action and resistance", Pharmachological Reviews, 55: 27-55 (2003).

Rekdal, Ø. et al., Relative Spatial Positions of Tryptophan and Cationic Residues in Helical Membrane-active Peptides Determine Their Cytotoxicity. J Biol Chem. 2012; 287(1):233-44.

* cited by examiner

| Peptide | Sequence | #AA | SI-1 |
|---|---|---|---|
| 8 | WRWRW-GG-RRRRRR | 13 | 21 |
| 9 | WRWRW-GG-RRRRR | 12 | 23 |
| 10 | WRWRW-GG-RRRR | 11 | >23 |
| 6b | WWWGGRRRRRRRRR | 14 | 9 |
| 6c | WRRRGRRWRGRRRW | 14 | >100 |
| 11 | WRRRRRWRRRRW | 12 | >73 |

A

B

C

SEQUENCE LISTING

```
<160> NUMBER OF SEQ ID NOS: 27

<210> SEQ ID NO 1
<211> LENGTH: 9
<212> TYPE: PRT
<213> ORGANISM: Artificial Sequence
<220> FEATURE:
```

```
<223> OTHER INFORMATION: Synthetic sequence
<220> FEATURE:
<221> NAME/KEY: MISC_FEATURE
<222> LOCATION: (8)..(8)
<223> OTHER INFORMATION: Diphenylalanine

<400> SEQUENCE: 1

Lys Lys Trp Trp Lys Lys Trp Xaa Lys
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Diphenylalanine
<220> FEATURE:
<221> NAME/KEY: MISC_FEATURE
<222> LOCATION: (9)..(9)
<223> OTHER INFORMATION: Amidated lysine

<400> SEQUENCE: 2

Trp Lys Lys Trp Xaa Lys Lys Trp Xaa
1               5

<210> SEQ ID NO 3
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Amino acid that is not cationic and is not
      tryptophan
<220> FEATURE:
<221> NAME/KEY: MISC_FEATURE
<222> LOCATION: (8)..(8)
<223> OTHER INFORMATION: Amino acid that is not cationic and is not
      tryptophan
<220> FEATURE:
<221> NAME/KEY: MISC_FEATURE
<222> LOCATION: (10)..(10)
<223> OTHER INFORMATION: Amino acid that is not cationic and is not
      tryptophan
<220> FEATURE:
<221> NAME/KEY: MISC_FEATURE
<222> LOCATION: (15)..(15)
<223> OTHER INFORMATION: Amino acid that is not cationic and is not
      tryptophan

<400> SEQUENCE: 3

Trp Xaa Arg Arg Arg Arg Arg Xaa Trp Xaa Arg Arg Arg Arg Xaa Trp
1               5                   10                  15

<210> SEQ ID NO 4
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Amino acid that is not cationic and is not
      tryptophan
<220> FEATURE:
<221> NAME/KEY: MISC_FEATURE
```

```
<222> LOCATION: (12)..(12)
<223> OTHER INFORMATION: Amino acid that is not cationic and is not
      tryptophan

<400> SEQUENCE: 4

Trp Xaa Arg Arg Arg Arg Trp Arg Arg Arg Xaa Trp
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Amino acid that is not cationic and is not
      tryptophan
<220> FEATURE:
<221> NAME/KEY: MISC_FEATURE
<222> LOCATION: (7)..(7)
<223> OTHER INFORMATION: Amino acid that is not cationic and is not
      tryptophan

<400> SEQUENCE: 5

Arg Arg Arg Arg Xaa Trp Xaa Arg Arg Arg Arg Trp
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Amino acid that is not cationic and is not
      tryptophan
<220> FEATURE:
<221> NAME/KEY: MISC_FEATURE
<222> LOCATION: (7)..(7)
<223> OTHER INFORMATION: Amino acid that is not cationic and is not
      tryptophan

<400> SEQUENCE: 6

Lys Lys Lys Lys Xaa Trp Xaa Lys Lys Lys Lys Trp
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Amino acid that is not cationic and is not
      tryptophan
<220> FEATURE:
<221> NAME/KEY: MISC_FEATURE
<222> LOCATION: (7)..(7)
<223> OTHER INFORMATION: Amino acid that is not cationic and is not
      tryptophan

<400> SEQUENCE: 7

Lys Arg Lys Arg Xaa Trp Xaa Lys Arg Lys Arg Trp
1               5                   10
```

```
<210> SEQ ID NO 8
<211> LENGTH: 16
<212> TYPE: PRT
<213> ORGANISM: Artificial Sequence
<220> FEATURE:
<223> OTHER INFORMATION: Synthetic peptide

<400> SEQUENCE: 8

Trp Gly Arg Arg Arg Arg Arg Gly Trp Gly Arg Arg Arg Arg Gly Trp
1               5                   10                  15

<210> SEQ ID NO 9
<211> LENGTH: 23
<212> TYPE: PRT
<213> ORGANISM: Artificial Sequence
<220> FEATURE:
<223> OTHER INFORMATION: Synthetic peptide

<400> SEQUENCE: 9

Lys Leu Ala Lys Leu Ala Lys Lys Leu Ala Lys Leu Ala Lys Gly Gly
1               5                   10                  15

Arg Arg Arg Arg Arg Arg Arg
            20

<210> SEQ ID NO 10
<211> LENGTH: 10
<212> TYPE: PRT
<213> ORGANISM: Artificial Sequence
<220> FEATURE:
<223> OTHER INFORMATION: Synthetic peptide

<400> SEQUENCE: 10

Trp Gly Gly Arg Arg Arg Arg Arg Arg Arg
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthetic peptide

<400> SEQUENCE: 11

Arg Trp Gly Gly Arg Arg Arg Arg Arg Arg Arg
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic peptide

<400> SEQUENCE: 12

Trp Arg Trp Gly Gly Arg Arg Arg Arg Arg Arg Arg
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Synthetic peptide

<400> SEQUENCE: 13

Arg Trp Arg Trp Gly Gly Arg Arg Arg Arg Arg Arg Arg
1               5                   10
```

<210> SEQ ID NO 14
<211> LENGTH: 14
<212> TYPE: PRT
<213> ORGANISM: Artificial Sequence
<220> FEATURE:
<223> OTHER INFORMATION: Synthetic peptide

<400> SEQUENCE: 14

Trp Arg Trp Arg Trp Gly Gly Arg Arg Arg Arg Arg Arg Arg
1               5                   10

<210> SEQ ID NO 15
<211> LENGTH: 15
<212> TYPE: PRT
<213> ORGANISM: Artificial Sequence
<220> FEATURE:
<223> OTHER INFORMATION: Synthetic peptide

<400> SEQUENCE: 15

Arg Trp Arg Trp Arg Trp Gly Gly Arg Arg Arg Arg Arg Arg Arg
1               5                   10                  15

<210> SEQ ID NO 16
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: (2,5,7-tri-tert-butyl)tryptophan

<400> SEQUENCE: 16

Trp Arg Xaa Gly Gly Arg Arg Arg Arg Arg Arg Arg
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: (2,5,7-tri-tert-butyl)tryptophan
<220> FEATURE:
<221> NAME/KEY: MISC_FEATURE
<222> LOCATION: (3)..(3)
<223> OTHER INFORMATION: (2,5,7-tri-tert-butyl)tryptophan

<400> SEQUENCE: 17

Xaa Arg Xaa Gly Gly Arg Arg Arg Arg Arg Arg Arg
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Synthetic peptide

<400> SEQUENCE: 18

Trp Arg Trp Arg Trp Gly Gly Arg Arg Arg Arg Arg Arg
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Synthetic peptide

<400> SEQUENCE: 19

Trp Arg Trp Arg Trp Gly Gly Arg Arg Arg Arg
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic peptide

<400> SEQUENCE: 20

Trp Arg Trp Arg Trp Gly Gly Arg Arg Arg Arg
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Synthetic peptide

<400> SEQUENCE: 21

Trp Trp Trp Gly Gly Arg Arg Arg Arg Arg Arg Arg Arg
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Synthetic peptide

<400> SEQUENCE: 22

Trp Arg Arg Arg Gly Arg Arg Trp Arg Gly Arg Arg Arg Trp
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthetic peptide

<400> SEQUENCE: 23

Trp Arg Arg Arg Arg Arg Trp Arg Arg Arg Trp
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (14)..(14)
<223> OTHER INFORMATION: Arginine with an amidated C terminus

<400> SEQUENCE: 24

Trp Arg Trp Arg Trp Gly Gly Arg Arg Arg Arg Arg Arg Xaa

```
<210> SEQ ID NO 25
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (12)..(12)
<223> OTHER INFORMATION: Tryptophan with an amidated C terminus

<400> SEQUENCE: 25

Trp Arg Arg Arg Arg Arg Trp Arg Arg Arg Arg Xaa
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Synthetic peptide

<400> SEQUENCE: 26

Trp Arg Trp Arg Trp Gly Gly Lys Lys Lys Lys Lys Lys Lys
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (6)..(7)
<223> OTHER INFORMATION: Amino acid that is not cationic and is not
      tryptophan

<400> SEQUENCE: 27

Trp Arg Trp Arg Trp Xaa Xaa Arg Arg Arg Arg Arg Arg Arg
1               5                   10
```

US 10,287,320 B2

ANTI-LYMPHOMA PEPTIDES

CROSS-REFERENCE TO RELATED APPLICATIONS

This application is a U.S. National Phase Application of International Application No. PCT/EP2015/052333, filed Feb. 4, 2015, which claims priority to British Patent Application No. 1401877.4, filed Feb. 5, 2014, the contents of each are hereby incorporated by reference in their entirety.

Reference to Sequence Listing

The Sequence Listing submitted herewith as a text file named "04150_0084U1_Sequence_Listing," created on Aug. 2, 2016, and having a size of 12,288 bytes is hereby incorporated by reference pursuant to 37 C.F.R. § 1.52(e)(5).

The present invention relates to novel peptides and to their use in the treatment of solid tumours, in particular lymphoma.

Lymphoma typically presents as a solid tumour of lymphoid cells. Malignant T or B lymphocytes or natural killer cells often originate in a lymph node, appearing as enlargement (tumour) of the node. Lymphoma may also develop in the spleen, bone marrow, skin, brain, bowels and bone.

In 2011 the number of US citizens living with or in remission from lymphoma was above six hundred and fifty thousand, making it the seventh most common cancer in the country. The two main types of lymphoma are Hodgkins (HL) and non-Hodgkins (NHL) and both show a strong correlation with age. Whereas, NHL is generally associated with older patients, HL is mostly diagnosed in young adults. Owing to modern treatments (chemotherapy, radiation or a combination of both) the prognosis for lymphoma has improved in the last years. However, several side effects are still associated with treatment, many of which are long term and serious (e.g. formation of second cancers). Although many of these side effects, for example the loss of fertility, might be an acceptable trade-off for older patients, they can have a severe impact on the life of younger patients. Efforts are, therefore, ongoing to develop new drugs and treatment strategies that will improve the long term prognosis for patients.

During the last decade our group has been developing a novel strategy for the intralesional treatment of solid tumors using α-helical cationic amphipathic peptides (CAP's). The rationale underlying this approach is that cancer cell membranes are often enriched with negatively charged macromolecules due to the overexpression of, for example, phosphatidyl serine, and sialic acid. This increase in anionic character makes cancer cells more amenable to ionic interactions with positively charged CAP's than their non-cancerous counterparts. The initial ionic interaction is followed by membrane disruption and, ultimately, the semi-selective lysis of the cancer cells. A peptide consisting of only nine amino acids, LTX-315 (Lys-Lys-Trp-Trp-Lys-Lys-Trp-Dip-Lys, SEQ ID NO:1), is being tested by Lytix Biopharma AS against different types of solid tumors in clinical trials (phase I).

However, the treatment of lymphoma tumors with CAP's may be more challenging than with other types of solid tumors. Whereas most solid tumors present a well-defined target, lymphomas are often more diffuse in character, containing large numbers of normal lymphocytes. The limited selectivity of CAP's could therefore lead to unacceptable levels of collateral damage to normal lymphocytes, other immune cells, and the surrounding healthy tissue. A more selective approach may therefore be needed for lymphoma treatment.

Berge et al. (Cancer Immunol Immunother (2010) 59: 1285-1294) have shown that intralesional treatment with CAP's can lead to regression of a murine lymphoma and initiation of a protective immune response but these molecules (e.g. W-K-K-W-Dip-K-K-W-K-amide, SEQ ID NO:2) are not particularly selective for the target cancer cells.

Thus there is a need for alternative or improved anti-lymphoma therapies which utilise an effective yet selective agent which can be economically manufactured and formulated. Preferably the agent will have a direct anti-tumour effect and a protective effect against recurrence and metastasis by inducing specific immunity.

In addressing these needs the present inventors have produced and tested a novel class of peptide with anti-lymphoma activity.

Thus, according to a first aspect, the present invention provides a peptide which:
(i) consists of 10 to 16 amino acids;
(ii) has at least 8 cationic amino acids with either
    (a) a side chain comprising a guanidinium group, or
    (b) a side chain comprising an amino group, of which no more than 7 are consecutive; and
(iii) has 2 or 3 tryptophan residues which are not both, or all, consecutive;
or a peptidomimetic of said peptide.

According to a preferred aspect, the present invention provides a peptide which:
(i) consists of 10 to 16 amino acids;
(ii) has at least 8 amino acid residues with a side chain comprising a guanidinium group, of which no more than 7 are consecutive; and
(iii) has 2 or 3 tryptophan residues which are not both, or all, consecutive;
or a peptidomimetic of said peptide.

Peptides of the present invention may be cyclic, whether cyclisation involves the amino and/or the carboxy terminus or one or more amino acid side chains, but will preferably be linear. Likewise, peptidomimetics of the present invention may also be cyclic molecules but preferably are linear. In general, features and preferred embodiments described in relation to the peptides of the invention apply, mutatis mutandis, to peptidomimetics of the invention.

Preferred peptides have 12 to 15 or 16 amino acids and 9 or more e.g. 9 or 10 cationic amino acids as defined above. Preferred peptides have 3 tryptophan (Trp or W according to the accepted 3 and 1 letter codes) residues. Preferably the peptides have only these two types of amino acid but peptides may also contain other amino acids which act as a spacer between Trp residues and the cationic residues. Thus the peptide may also contain 1-6 other residues, preferably 1, 2, 3 or 4 other residues (conveniently referred to as X residues). These residues, which may be the same or different, are preferably small (e.g. no more than 4 non-hydrogen atoms in the side chain), non-charged and non-polar. Preferred residues include glycine (G) and 6-aminohexanoic acid. Thus in embodiments containing such residues, the peptides will typically comprise a residue X adjacent to both a Trp residue and a cationic amino acid as defined herein, each Trp residue may have an X residue adjacent to it. Examples of peptides incorporating X residues include:

WXRRRRRXWXRRRRXW (SEQ ID NO: 3)

WXRRRRWRRRRXW (SEQ ID NO: 4)

RRRRXWXRRRRW (SEQ ID NO: 5)

KKKKXWXKKKKW (SEQ ID NO: 6)

KRKRXWXKRKRW (SEQ ID NO: 7)

and

WRWRWXXRRRRRRR (SEQ ID NO: 27)

Preferred amino acid residues with a side chain comprising a guanidinium group are arginine (Arg or R according to the accepted 3 and 1 letter codes used herein) and homoarginine. A guanidinium group is the protonated cation of guanidine (it is protonated under physiological conditions) and can be represented by the following formula $RNHC(NH_2)_2^+$. For convenience herein amino acid residues with a side chain comprising a guanidinium group, are referred to as guanidinium containing residues.

'Side chain' refers to the variable group (often called the R group) of an amino acid, typically attached to the α-carbon but which may be attached to the β-carbon in a β-amino acid and so on.

Preferred amino acids with a side chain comprising an amino group are lysine (Lys or K according to the 3 and 1 letter codes) and derivatives thereof, such as aminocaproic acid and ornithine (thus the side chain may contain more than one amino group). The amino group (—$NH_2$) or groups is/are typically attached to a linear (or branched) alkyl group (e.g. $C_2$-$C_8$ alkyl) and the side chain typically contains no other heteroatoms.

If the peptide has 3 Trp residues these are preferably dispersed in the peptide so that no 2 Trp residues are adjacent. Preferably there will be at least 2, more preferably at least 3 cationic amino acids separating any 2 Trp residues.

In some preferred embodiments a Trp residue will be found at the N and/or C terminus of the peptide or peptidomimetic.

Preferably the peptides of the invention have no more than 6, more preferably no more than 5 consecutive cationic amino acids as defined herein.

The peptides and peptidomimetics of the invention include all enantiomeric forms, in particular the molecules of the invention may comprise D and/or L forms of the amino acids.

The peptides of the invention preferably contain at least 8 guanidinium containing residues and preferably all cationic amino acids are of this type. Alternatively, the peptide may have all its cationic amino acids of the type which comprise an amino group in the side chain (e.g. Lys) or it may have a mixture of the two types of cationic amino acid, e.g. 1-3 cationic amino acids with a side chain comprising an amino group.

In some preferred embodiments the molecules of the invention contain one block of at least 5 consecutive cationic amino acids as defined above, optionally also a second block of at least 3 consecutive such cationic amino acids. Preferably these are all guanidinium containing residues.

The molecules of the invention may be amidated, esterified or in salt form and may be administered in these forms.

Suitable physiologically acceptable salts are well known in the art and include salts of inorganic or organic acids, preferred salts include trifluoroacetate, acetate and salts formed with HCl. The molecules may incorporate a modified N and/or C terminus. Preferred examples include acetylation at the N terminus to form an alkylated amine or incorporation of a thiol modification, e.g. to form a cysteamine group at the N terminus. The C terminus is conveniently amidated but may alternatively form an ester, amidation of the C terminus is preferred. Thus 'peptides' include peptides with a modified N and/or C terminus and peptidomimetics may be similarly modified.

The cationic residues may be non-genetically coded and the peptide may contain other non-genetically coded amino acids, i.e. amino acids other than the standard 20 amino acids of the genetic code may be included within the X residues.

A peptidomimetic is typically characterised by retaining the polarity, three dimensional size and functionality (bioactivity) of its peptide equivalent but wherein one or more of the peptide bonds have been replaced, often by more stable linkages. By 'stable' is meant more resistant to enzymatic degradation by hydrolytic enzymes. Generally, the bond which replaces the amide bond (amide bond surrogate) conserves many of the properties of the amide bond, e.g. conformation, steric bulk, electrostatic character, possibility for hydrogen bonding etc. Chapter 14 of "Drug Design and Development", Krogsgaard, Larsen, Liljefors and Madsen (Eds) 1996, Horwood Acad. Pub provides a general discussion of techniques for the design and synthesis of peptidomimetics. Suitable amide bond surrogates include the following groups: N-alkylation (Schmidt, R. et al., Int. J. Peptide Protein Res., 1995, 46,47), retro-inverse amide (Chorev, M and Goodman, M., Acc. Chem. Res, 1993, 26, 266), thioamide (Sherman D. B. and Spatola, A. F. J. Am. Chem. Soc., 1990, 112, 433), thioester, phosphonate, ketomethylene (Hoffman, R. V. and Kim, H. O. J. Org. Chem., 1995, 60, 5107), hydroxymethylene, fluorovinyl (Allmendinger, T. et al., Tetrahydron Lett., 1990, 31, 7297), vinyl, methyleneamino (Sasaki, Y and Abe, J. Chem. Pharm. Bull. 1997 45, 13), methylenethio (Spatola, A. F., Methods Neurosci, 1993, 13, 19), alkane (Lavielle, S. et. al., Int. J. Peptide Protein Res., 1993, 42, 270) and sulfonamido (Luisi, G. et al. Tetrahedron Lett. 1993, 34, 2391).

The peptidomimetic compounds of the present invention will typically have identifiable sub-units which are approximately equivalent in size and function to amino acids, e.g. to guanidinium containing residues such as Arg, or Trp. The term 'amino acid' may thus conveniently be used herein to refer to the equivalent sub-unit of a peptidomimetic compound.

As is discussed in the text book referenced above, as well as replacement of amide bonds, peptidomimetics may involve the replacement of larger structural moieties with di- or tripeptidomimetic structures and in this case, mimetic moieties involving the peptide bond, such as azole-derived mimetics may be used as dipeptide replacements.

Peptidomimetics and thus peptidomimetic backbones wherein just the amide bonds have been replaced as discussed above are, however, preferred.

Suitable peptidomimetics include reduced peptides where the amide bond has been reduced to a methylene amine by treatment with a reducing agent e.g. borane or a hydride reagent such as lithium aluminium-hydride. Such a reduction has the added advantage of increasing the overall cationicity of the molecule.

Other peptidomimetics include peptoids formed, for example, by the stepwise synthesis of amide-functionalised polyglycines. Some peptidomimetic backbones will be readily available from their peptide precursors, such as peptides which have been permethylated, suitable methods are described by Ostresh, J. M. et al. in Proc. Natl. Acad. Sci. USA (1994) 91, 11138-11142. Strongly basic conditions will favour N-methylation over O-methylation and result in methylation of some or all of the nitrogen atoms in the peptide bonds and the N-terminal nitrogen.

Preferred peptidomimetic backbones include polyesters, polyamines and derivatives thereof as well as substituted alkanes and alkenes. The peptidomimetics will preferably have N and C termini which may be modified as discussed herein.

β and γ amino acids as well as α amino acids are included within the term 'amino acids', as are N-substituted glycines. The compounds of the invention include beta peptides and depsipeptides.

The molecules described herein have been shown to combine good cytotoxicity against lymphoma cells in vitro and in vivo with selectivity for lymphoma cells. An adaptive immune response has also been shown through enhanced survival rates after rechallenge with lymphoma cells in a mouse model. Thus the molecules are of considerable therapeutic interest. This is supported not only by the efficacy data presented in Examples 1 to 3, but also the cardiotoxicity data of Example 4 which shows that the molecules of the invention do not adversely interact with the cardiovascular system.

In a further aspect, the present invention provides a pharmaceutical composition comprising a peptide or peptidomimetic of the invention as defined herein together with a pharmaceutically acceptable diluent, carrier or excipient.

In a further aspect, the present invention provides a peptide or peptidomimetic of the invention as defined herein or a pharmaceutical composition as defined herein for use in therapy.

In a further aspect, the present invention provides a peptide or peptidomimetic of the invention as defined herein or a pharmaceutical composition as defined herein for use in the treatment of tumours (a tumour) or cancer cells. Treatment includes preventing or reducing the growth, establishment, spread or metastasis of a tumour. Tumours treated according to the present invention will typically be solid and cancerous. Treatment includes prophylactic treatment, e.g. through the induction of specific immunity to an initially treated tumour which can prevent the establishment of a further tumour of the same or a similar type. Such prophylactic treatments may be secondary to treatment of a target tumour or may, in certain circumstances, be the primary purpose of treatment. Treated cancer cells will likewise have their growth and/or spread prevented or reduced.

Compositions, uses and treatment methods described herein may further comprise a second therapeutic agent, in particular a further anti-cancer agent or an agent which supports the efficacy of the peptides or peptidomimetics of the present invention. A further anti-cancer agent will typically be active against lymphoma.

The molecules described herein can be considered antitumoural, anticancer or antineoplastic agents. Cancer cells may exist within a tumour or may lack the morphological characteristics of a tumour, e.g. be circulating within the body.

The preferred cancer targets are lymphomas, e.g. Burkitt's lymphoma, diffuse large B cell lymphoma or cutaneous lymphoma. Both T- and B-lymphomas can be treated according to the present invention. In general solid tumours are treated and treatment is preferably intralesional, i.e. intratumoural.

In a further aspect, the present invention provides a method of treating a tumour or cancer cells, which method comprises administering to a subject a pharmaceutically effective amount of a peptide or peptidomimetic of the invention as defined herein. Typically the subject has been identified as being in need of the treatment, e.g. diagnosed as having cancer, in particular a lymphoma.

In a further aspect, the present invention provides the use of a peptide or peptidomimetic of the invention as defined herein in the manufacture of a medicament for the treatment of a tumour or of cancer cells.

Treatment, as mentioned above, includes a reduction in growth of the tumours, e.g. a reduction in size of the tumour, e.g. by at least 20%, preferably at least 30 or 50%, more preferably at least 70%. Treatment may lead to eradication of the tumour but treatment can be considered successful even without eradication of the tumour. The primary objective will be to increase life expectancy and/or to improve quality of life. Prognosis after a diagnosis of lymphoma can be estimated by clinicians and improved survival rates, whether at 1, 5 or 10 years may be judged against data or expectations.

As discussed further in the Examples herein, the molecules of the invention operate in a caspase independent manner which, without wishing to be bound by theory, seems to be limited to the generation of a strong protective immune response. Signs of necrosis are seen including cell lysis, but the scanning electron micrographs are not analogous to those seen with classic CAP's which are lytic against a wide range of solid tumours, e.g. LTX-315. In the case of the molecules of the present invention a more violent event is suggested and there is some specificity for lymphoma cells over other cancer cells. Without wishing to be bound by theory, it is suggested that the mode of action for these molecules is linked with an inherent property of lymphoid cells. A possible explanation might be that lymphoid cells are well endowed with microvilli which provide an increased cell surface area, allowing for a higher ratio of interaction between peptides and cells. Analysis of preferred peptides of the invention suggest they are not likely to have a significant lytic effect on cell membranes directly but could instead penetrate the cell membrane. Observations suggest cell death is not a result of mitochondrial lysis. Therefore the molecules of the invention may function through a form of programmed cell death which is independent of caspase activation.

Thus, alternatively viewed, the present invention provides a peptide or peptidomimetic of the invention as defined herein or a pharmaceutical composition as defined herein for use in treating lymphoma, particularly for use in treating lymphoma in a caspase-independent way.

The molecules of the invention may be administered by any convenient means, in particular by enteral, parenteral or topical routes. Parenteral routes are preferred and intratumoural (intralesional) administration is particularly preferred. Topical administration may be appropriate in certain cases, in particular when treating a cutaneous lymphoma. Thus administration may be local, e.g. topical or intratumoural, or systemic.

The skilled man will be able to formulate the molecules of the invention into pharmaceutical compositions that are adapted for these routes of administration according to any of the conventional methods known in the art and widely described in the literature.

The active ingredient may be incorporated, optionally together with other active agents, with one or more conventional carriers, diluents and/or excipients, to produce conventional galenic preparations such as tablets, pills, powders (e.g. inhalable powders), lozenges, sachets, cachets, elixirs, suspensions, emulsions, creams, foams, gels, solutions, syrups, aerosols (as a solid or in a liquid medium), lotions, ointments, soft and hard gelatine capsules, suppositories, sterile injectable solutions, sterile packaged powders, and the like.

Examples of suitable carriers, excipients, and diluents are lactose, dextrose, sucrose, sorbitol, mannitol, starches, gum acacia, calcium phosphate, inert alginates, tragacanth, gelatine, calcium silicate, microcrystalline cellulose, polyvinylpyrrolidone, cellulose, water syrup, water, water/ethanol, water/glycol, water/polyethylene, hypertonic salt water, glycol, propylene glycol, methyl cellulose, methylhydroxybenzoates, propyl hydroxybenzoates, talc, magnesium stearate, mineral oil or fatty substances such as hard fat or suitable mixtures thereof. Preferred excipients and diluents are mannitol and hypertonic salt water (saline).

The compositions may additionally include lubricating agents, wetting agents, emulsifying agents, suspending agents, preserving agents, sweetening agents, flavouring agents, and the like.

Parenterally administrable forms should be sterile and free from physiologically unacceptable agents, and should have low osmolarity to minimize irritation or other adverse effects upon administration and thus solutions should preferably be isotonic or slightly hypertonic, e.g. hypertonic salt water (saline). Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405-1412 and 1461-1487 (1975) and The National Formulary XIV, 14th ed. Washington: American Pharmaceutical Association (1975). The solutions can contain preservatives, antimicrobial agents, buffers and antioxidants conventionally used for parenteral solutions, excipients and other additives which are compatible with the biopolymers and which will not interfere with the manufacture, storage or use of products.

A more sophisticated delivery vehicle, e.g. liposomes, may be used, in particular when delivery is systemic, the liposome encasing peptides of the invention in aqueous solution.

In medical applications, the peptide or mimetic may conveniently be administered at concentrations of 5-500 mg/l, preferably 20-100 mg/l, e.g. 40-60 mg/l.

The molecules described herein may be synthesised in any convenient way. Generally the reactive groups present (amino and/or carboxyl terminus and some side chains) will be protected during overall synthesis.

Methods of peptide synthesis are well known in the art but for the present invention it may be particularly convenient to carry out the synthesis on a solid phase support (SPPS), such supports and associated techniques being well known in the art. In building up the peptides, one can in principle start either at the C-terminus or the N-terminus, although stepwise addition to a free N-terminus is preferred.

Methods for the synthesis of the molecules of the invention constitute a further aspect of the present invention. For example, in one embodiment there is provided a method of synthesising a molecule of the invention as defined herein, which method includes the generation of a molecule of the invention having one or more protecting groups attached thereto and then the removal of said protecting group(s). Preferably the molecule is formed on a solid support by stepwise addition of amino acids or equivalent sub-units and then, in either order, (i) any remaining protecting groups are removed and (ii) the peptide is removed from the solid support.

A wide choice of protecting groups for amino acids are known (see for example Isidro-Llobet et al. Chem. Rev. [2009] 109, 2455-2504). It will be appreciated that when a peptide is built up from the C-terminal end, an amine-protecting group will be present on the α-amino group of each new residue added and will need to be removed selectively prior to the next coupling step. Suitable amine protecting groups include t-butoxycarbonyl (also designated Boc) and 9-fluorenylmethoxy-carbonyl (also designated Fmoc). Fmoc based SPPS procedures, for example as described in the Examples, are preferred. These procedures may be automated and amino acids with Fmoc protected N-termini and any necessary side-chain protection are readily available. When Fmoc is used as the N-terminal protecting group, conveniently mild acid-labile protecting groups that are stable under basic conditions, such as Boc or benzyl groups may be used to protect reactive amino acid side chains.

A wide range of procedures exists for removing protecting groups. These must, however, be consistent with the synthetic strategy employed. The side chain protecting groups must be stable to the conditions used to remove the temporary α-amino protecting group prior to the next coupling step.

Dosage units containing the active molecules preferably contain 0.1-10 mg, for example 1.5 mg of the antitumour molecule of the invention. The pharmaceutical compositions may additionally comprise further active ingredients, including other cytotoxic or antitumour agents such as other antitumour peptides. Other active ingredients may include different types of cytokines e.g. IFN-γ, TNF, CSF and growth factors, immunomodulators, chemotherapeutics e.g. cisplatin or antibodies or cancer vaccines.

In employing such compositions systemically, the active molecule is present in an amount to achieve a serum level of the active molecule of at least about 5 μg/ml. In general, the serum level need not exceed 500 μg/ml. A preferred serum level is about 100 μg/ml. Such serum levels may be achieved by incorporating the bioactive molecule in a composition to be administered systemically at a dose of from 1 to about 10 mg/kg. In general, the molecule(s) need not be administered at a dose exceeding 100 mg/kg.

In a further aspect the present invention provides a molecule as defined herein and (b) a further antitumoural agent as a combined preparation for separate, simultaneous or sequential use in the treatment of a tumour or cancer cells or preventing or reducing the growth, establishment spread, or metastasis of a tumour.

The above description describes numerous features of the present invention and in most cases preferred embodiments of each feature are described. It will be appreciated that each preferred embodiment of a given feature may provide a molecule, use, method etc. of the invention which is preferred, both when combined with the other features of the invention in their most general form and when combined with preferred embodiments of other features. The effect of selecting multiple preferred embodiments may be additive or synergistic. Thus all such combinations are contemplated unless the technical context obviously makes them mutually exclusive or contradictory. In general each feature and preferred embodiments of it are independent of the other features and hence combinations of preferred embodiments may be presented to describe sub-sets of the most general definitions without providing the skilled reader with any new concepts or information as such.

The invention will now be described with reference to the following non-limiting Examples (including comparative examples) and with reference to the following figures:

FIG. 1. First activity/selectivity screen (MTT) with chimeric peptides against A20 cells. The five most active peptides (1b, 6a, 7, 4b and 4c) were tested against MRC-5 cells to determine selectivity. Peptide 6a was selected for further study. The $IC_{50}$ values shown are the average of three independent experiments done in triplicate.

Figure 2:
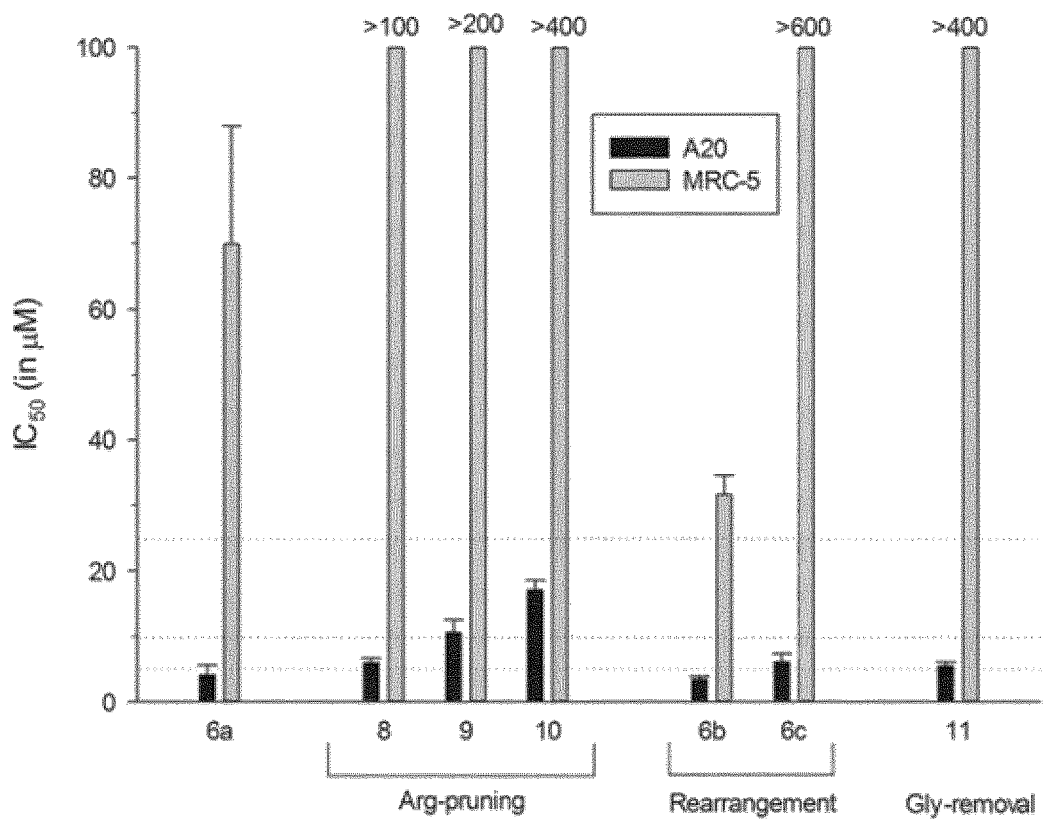

FIG. 2. Second activity/selectivity screen (MTT) for analogues of 6a against A20 lymphoma and MRC-5 fibroblast cells. Three rounds of modifications were done to shorten the peptide and increase selectivity without decreasing activity. Peptide 11 was selected for further study. The $IC_{50}$ values shown are the average of three independent experiments done in triplicate.

Figure 3:
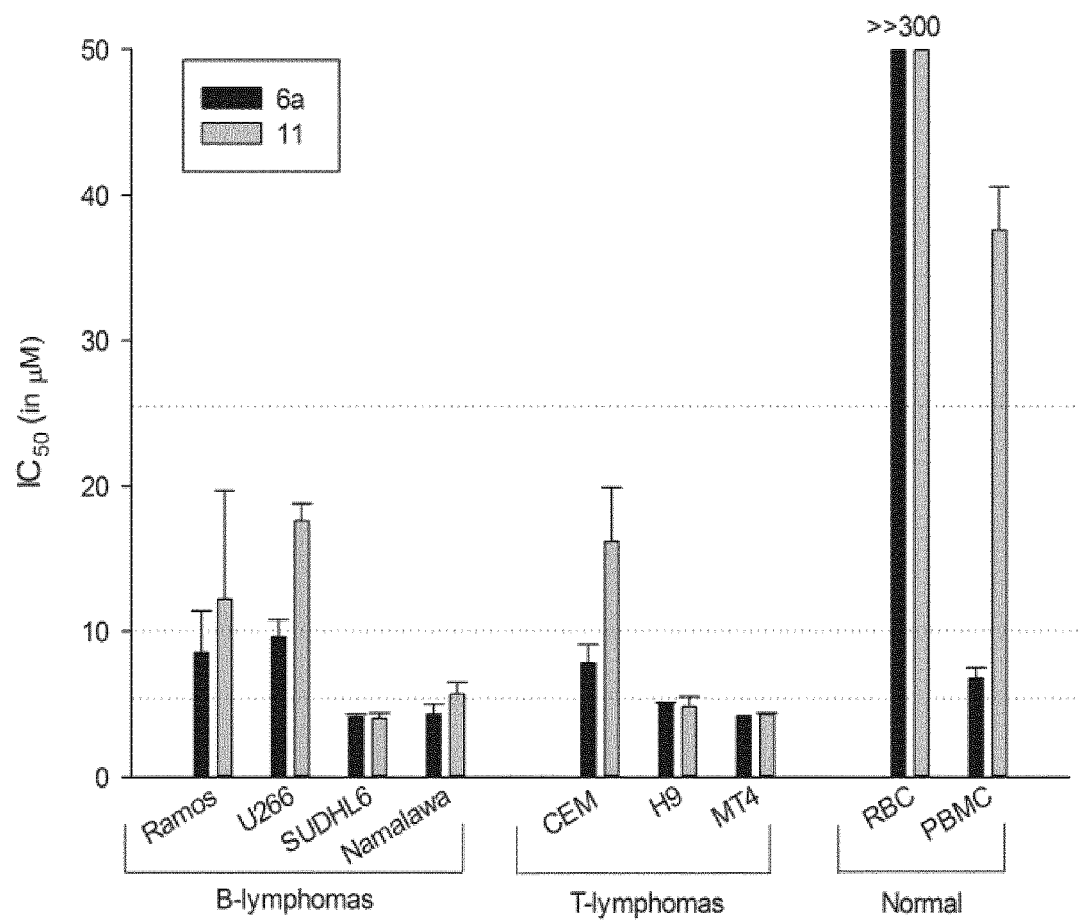

FIG. 3. Panel screen (MTT) against several lymphomas cell lines and red blood cells to determine overall activity and selectivity of peptide 6a and 11. The $IC_{50}$ values shown are average of three independent experiments done in triplicate, except for RBC (two independent experiments).

Figure 4:
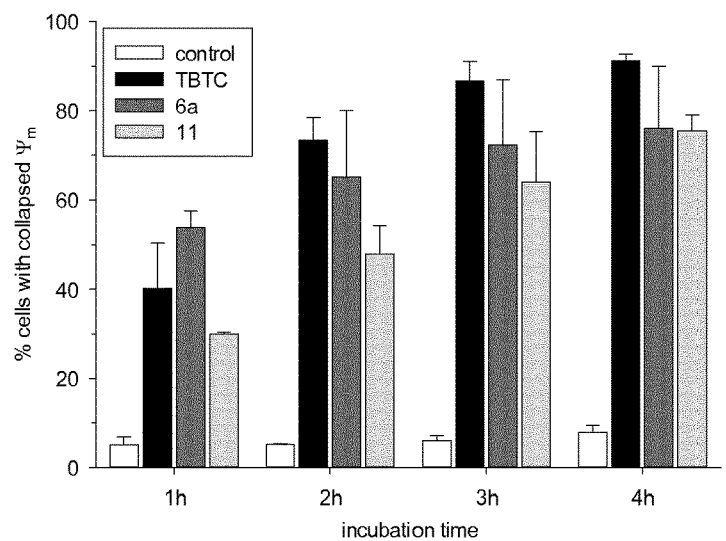
Figure 4:
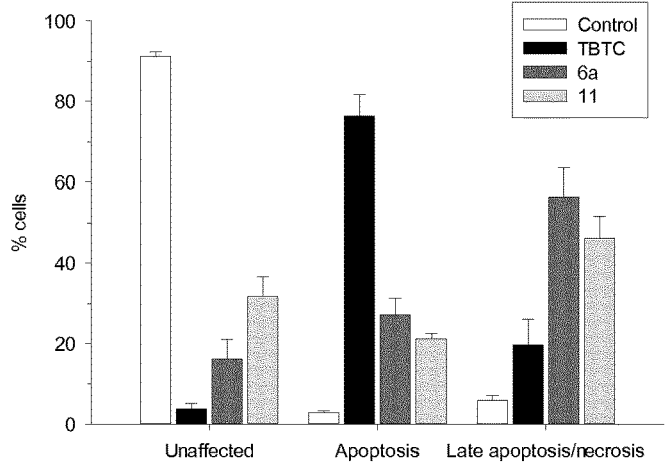
Figure 4:
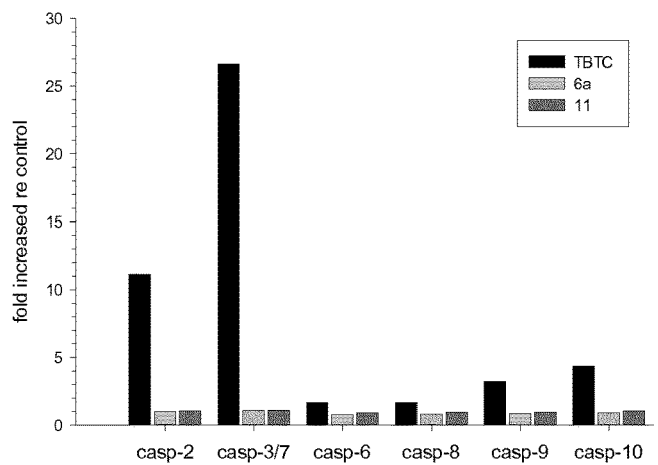

FIG. 4. Mechanism of action studies for 6a and 11. A20 cells were treated with peptides (at $IC_{50}$ concentration and TBTC was positive control in all cases. (A) Measuring effect of peptides on mitochondrial membrane potential using TMRE. Similar effect for both peptides after 4 hrs, but 6a is faster acting. (B) Inspecting the cell membrane for the presence of translocated phosphatidylserine and integrity by staining with AnnexinV-FITC and PI. Two thirds of affected cells show signs of membrane disruption. (C) Screening for the activation of caspase using fluorescently labeled substrates. Neither peptide induced activation of initiator/effector caspases during a 1 hour treatment. Results from A-C indicate a caspase independent mechanism of action where the integrity of the cell membrane is compromised.

Figure 5:
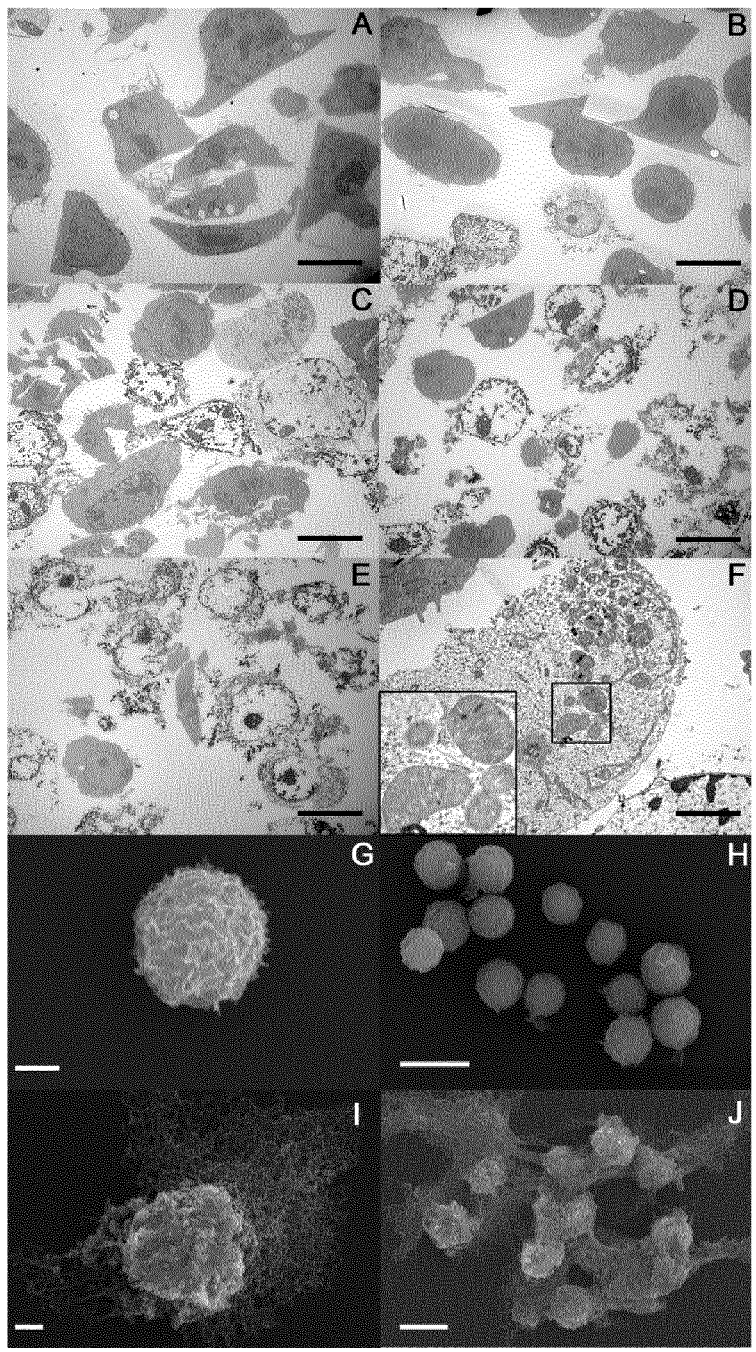

FIG. 5. Electron microscopy. (A and B) TEM micrographs of untreated Ramos cells. (C, D, and E) Time study—Ramos cells were treated with 6a and samples prepared at different time points. (F) A disintegrated cell with mostly intact mitochondria corroborating the results of the caspase screening. (G and H) SEM micrographs of untreated A20 cells. (I and J) After treatment with 6a. The same effect was seen over a broad concentration range (1-10×IC50).

Figure 6:
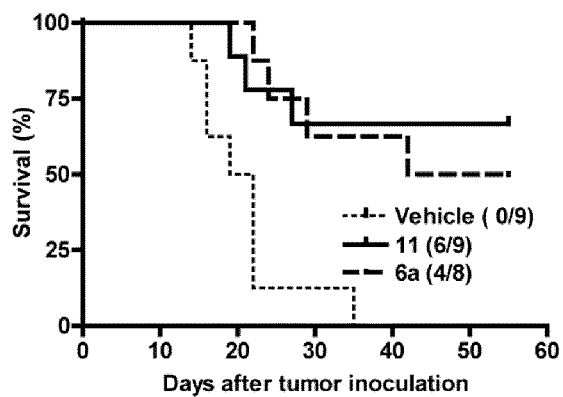

FIG. 6. Intratumoral effects of peptides 6a and 11. Survival curves were compared by the log-rank test.

Figure 7:
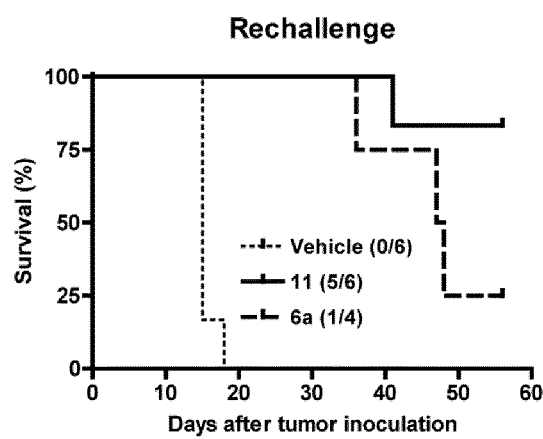

FIG. 7. Protective immune response after treatment with peptides 6a and 11. Survival curves were compared by the log-rank test.

Figure 8:
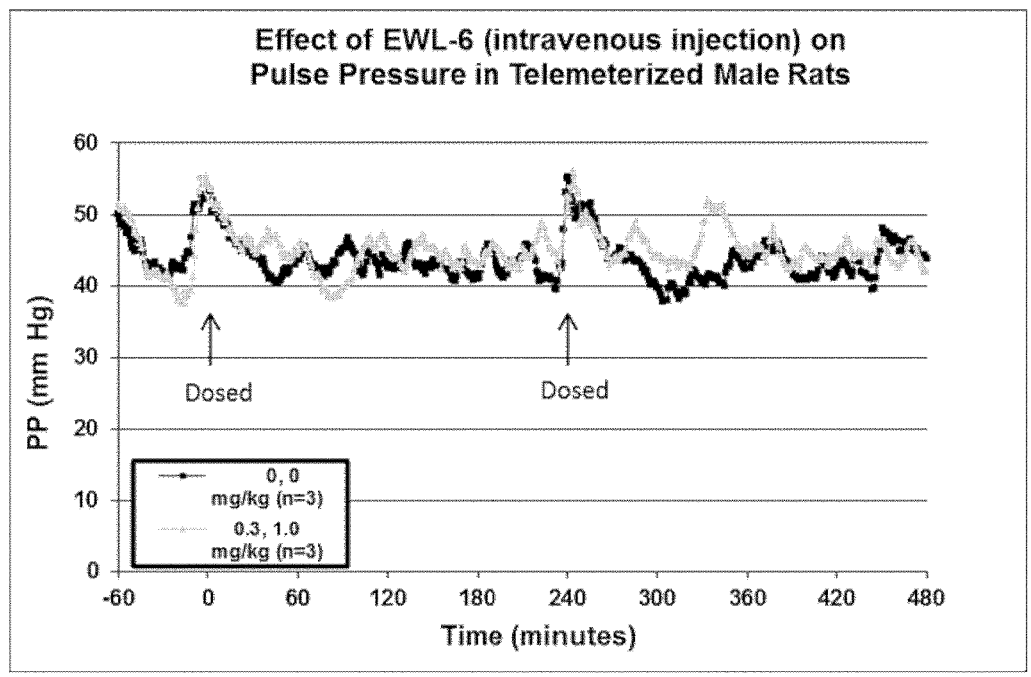

FIG. 8. Is a graph showing the effects on pulse pressure after administration of EWL-6 (WGRRRRRGWGR-RRRGW, SEQ ID NO:8) to telemeterized rats.

Figure 9:
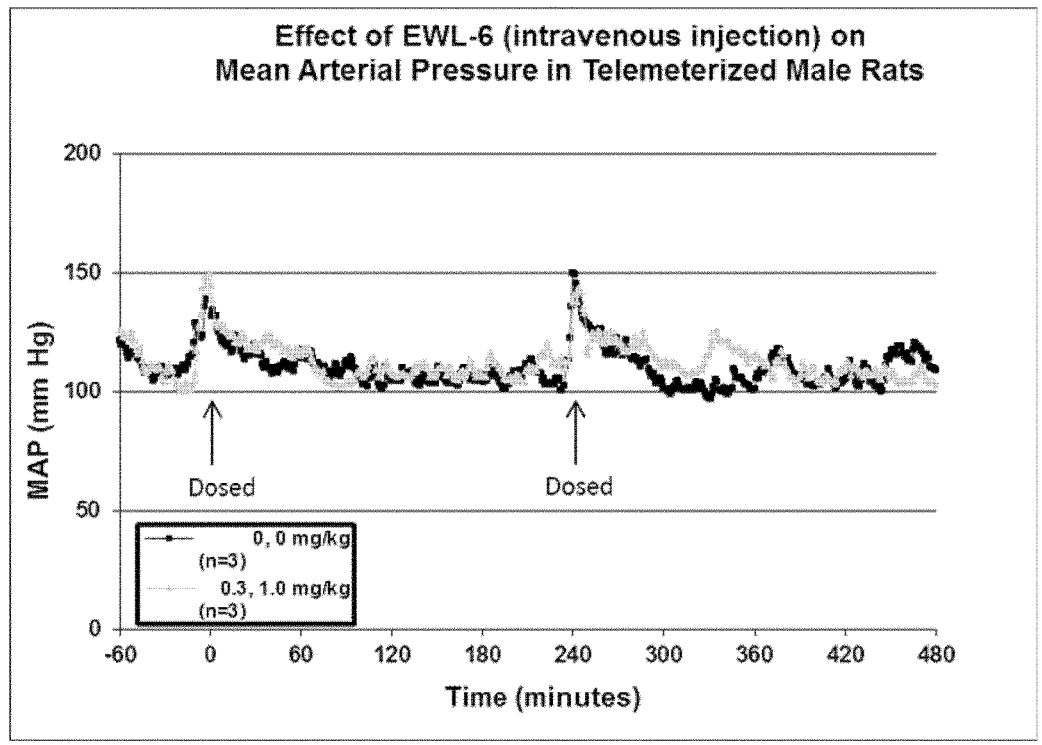

FIG. 9. Is a graph showing the effects on mean arterial pressure after administration of EWL-6 (SEQ ID NO:8) to telemeterized rats.

EXAMPLES

Example 1—In Vitro Studies

Materials and Methods

Chemicals and Reagents Used

Annexin V-FITC (Biovision), Propidium iodide (Sigma-Aldrich), Tributyltin chloride (Sigma-Aldrich), RPMI-1640 (Sigma-Aldrich), Tetramethylrhodamine ethyl ester perchlorate (Invitrogen), Hank's balanced salt solution (Sigma Aldrich), Caspase Fluorometric Substrate Set II Plus kit (Biovision)

Peptide Synthesis

All peptides were synthesized on a Tribute (Protein Technologies Inc.) instrument using standard Fmoc protocols and amino acid derivatives. The Fmoc-derivative of Tbt β-(2,5, 7-tri-tert-Butylindol-3-yl)alanine) was prepared as described in Haug et al. (2008) J. Med. Chem. 51(14) pp. 4306-14.

After synthesis the peptides were cleaved from the Rink Amide resin (Novabiochem) using a cocktail containing 95% TFA, 2.5% water and 2.5% triisopropylsilane over a period of 3 hours. The TFA was removed under vacuum and the fully deprotected and C-terminal amidated peptides precipitated with diethyl ether.

Peptide Purification and Characterization

The crude material was purified on a Waters 600E semi-preparative RP-HPLC system using a C18 (20×250 mm, 5 μm, 100 Å) Inersil ODS-3 column from GL Sciences. The purity of peptides were determined with analytical RP-HPLC (Waters 2695 system) using a C18 (4.6×250 mm, 5 μm, 100 Å) Sunfire column. The analyses were done on a gradient of 0-50% B over 30 minutes with a flow rate of 1.0 ml/min and peak detection set at 214 nm. All HPLC solvents (water and acetonitrile) contained 0.1% TFA. All peptides tested had a purity of >95%.

The molecular mass of the purified peptides were determined by MALDI-ToF (MALDI micro MX, Waters Micromass MS Technologies). The mass spectra were obtained with positive ion (reflector) mode with α-cyano-4-hydroxycinnamic acid as matrix. The purified peptides were then freeze dried (Model) and stored at −20° C. until further use.

Cell Culturing

All cell lines used were tested for *mycoplasma* and cultured in 5% CO2 at 37° C. (Hera Cell 150 incubator, Thermo Electron Corp.). The different cell lines (including ATCC and passage numbers) used is listed in the table below:

| | | Cell lines | | |
|---|---|---|---|---|
| Name | Species | Cell type (Disease) | ATCC# | Passage # |
| A20 | Murine | B lymphocyte (Reticulum cell sarcoma) | Unknown | 7-33 |
| Ramos | Human | B lymphocyte (Burkitt's lymphoma) | Unknown | 5-10 |
| U266 | Human | B lymphocyte (Myeloma) | TIB-196 | Unknown |
| SUDHL6 | Human | B lymphocyte (Large cell lymphoma) | (b) | Unknown |
| Namalawa | Human | B lymphocyte (Burkitt's lymphoma) | (a) | Unknown |
| CEM | Human | T lymphoblast (Lymphoblastic leukemia) | (a) | Unknown |

-continued

| Cell lines | | | | |
|---|---|---|---|---|
| Name | Species | Cell type (Disease) | ATCC# | Passage # |
| H9 | Human | T cells | (a) | Unknown |
| MT4 | Human | T cells | (a) | Unknown |
| MRC-5 | Human | Normal lung fibroblast | CCL-171 | 25-36 |
| RBC | Human | Normal red blood cells | n.a.[c] | n.a.[c] |

[a]Obtained from Dr. Michael Norcross, Center of Drug Evaluation and Research, F.D.A., Bethesda, MD, U.S.A.
[b]Kindly provided by Dr. Mark Raffeld, National Cancer Institute, NIH, Bethesda, MD, USA.
[c]Isolated from blood of healthy donors and used immediately.

RBC Isolation and Hemolysis Assay

Blood samples taken from two healthy donors were heparinized and washed. The RBC's were then resuspended in PBS and diluted to 10% hematocrit. The RBC's were treated immediately with the peptides for a period of an hour at 37° C. After treatment the cells were spun down and 100 µL of the supernatant transferred to a 96-well plate. The absorbance was read at 405 nm.

Cytotoxicity Assay

The first screen against A20 and MRC-5 was done manually, while the lymphoma panel screen were done at Marbio (Tromsø) using an automated platform (Biomek NX, Beckman Coulter).

Cells were automatically counted (Z1 Coulter Particle Counter, Beckman Coulter) and the cells seeded out in 96-well plates. The plates were incubated for at least 16 hours before the start of the assay.

The growth media was removed and the cells washed once with 100 µL assay media (RPMI-1640). Cells were then treated with 100 µL peptide solution (concentration varying from 500-10 µg/mL) for 4 hrs. Normal assay media and assay media containing 0.1% Triton were used as negative and positive controls, respectively. After this period 10 µL of a MTT solution (5 mg/mL) was added to each well and the plate incubated for a further 2 hrs. Following this 70 µL of the media was carefully removed and 100 µL acidified isopropanol added. The formed formazan crystals were dissolved by agitating the cells with a micropipette and by shaking (30 mins). The absorbance of the reduced MTT (formazan) was read on Versa Max Microplate Reader (Molecular Devices) at 590 nm. All assays, unless mentioned otherwise, were done in triplicate.

Annexin V-FITC/PI Assay

The assay was performed according to the MTT assay and adapted from Tørfoss et al. in J. Pept. Sci 2012, 18(3): p. 170-6). Briefly, A20 cells were used in a final concentration of $3 \times 10^5$ cells/ml and the cells were seeded in RPMI-1640 medium containing compounds 6a and 11 (at $IC_{50}$ concentrations). As control for apoptosis induction cells treated with 0.5 µM TBTC were used. Untreated cells were used as negative control. After 1 h incubation the cells were collected, centrifuged and resuspended to $1 \times 10^6$ cells/mL in 10 mM HEPES/NaOH buffer, containing 0.14M NaCl and 2.5 mM $CaCl_2$.

The cells were subsequently stained with annxin V-FITC and propidium iodide (PI) and incubated for 10 min in the dark at room temperature. The stained cells were analyzed using the FL-1 and FL-3 channel of a FACSCalibur (Becton & Dickenson, San Jose, Calif., USA) flow cytometer.

Mitochondrial Membrane Potential ($\Delta\psi m$) Assessment

The assay was adapted from Ausbacher et al. (2012) Biochem-Biophys. Acta, 1818(11) p. 2917-25. Briefly, the A20 cells ($3 \times 10^5$ cells/ml) were seeded in 12-well plates and incubated for 1 h-4 h with 6a and 11 at their determined $IC_{50}$ values. As positive control TBTC (0.1 µM) treated cells were used and untreated cells as negative control. TMRE was added to a final concentration of 100 nM 20 min before the respective experiment endpoints. Subsequently, the cells were collected and resuspended in HBSS to a final concentration of $1 \times 10^6$ cells/ml and analyzed with the FL-2 channel of a FACSCalibur flow cytometer Caspase Activity Screening To detect involvement of caspase 2, -3/7, -6, -8, -9, and -10, an activity screen was performed using the Caspase Fluorometric Substrate Set II Plus kit (Biovision Research Products, Mountain View, Calif., USA) according to Ausbacher et al. (supra) Briefly, A20 cells ($3 \times 10^5$ cells/nil) were treated with $1 \times IC_{50}$ of 6a, $1 \times IC_{50}$ of 11 or 0.5 µM TBTC for 1 h. Subsequently the cells were lysed and the lysate were supplemented with reaction buffer as well as DL-dithiothretiol solution. The 7-amino-4-trifluoro methylcoumarin labeled caspase substrates were added, incubated at 37° C. for 2 h and analyzed on a fluorescence plate reader (SpectraMAX Gemini EM, Molecular devices, Sunnyvale, Calif., USA). Caspase activity was determined by comparing the fluorescence intensities of treated and untreated control samples.

Transmission Electron Microscopy (TEM)

Ramos cells ($2 \times 10^5$ cells/nil) were suspended in peptide containing serum free RPMI-1640 medium and transferred in culture flasks (NUNC Easy flask 25 cm2, Thermo Fischer Scientific, Langenselbold, Germany). The peptide concentrations were chosen according to the previously determined $IC_{50}$ values. All cells were pre-fixed with Karnovsky's cacodylate-buffered (pH 7.2) formaldehyde-glutaraldehyde fixative at 4° C. overnight. The fixative was replaced by Karnovsky's buffer and post-fixated with 1% osmium tetroxide. After dehydration in a graded series of ethanol, samples were infiltrated with a 1:1 mixture of acetonitrile and epon resin (AGAR 100, DDSA, MNA and DMP-30) over night. Pure resin was added the following day and then polymerized for 24 h. Ultrathin sections were prepared and placed on formvar, carbon-stabilized copper grids. The samples were stained and contrasted with uranyl acetate (5%) and Reynold's lead citrate. Samples were analyzed on a JEOL-1010 transmission electron microscope (JEOL, Akaishima, Japan). An Olympus Morada side-mounted TEM CCD camera (Olympus soft imaging solutions GmbH, Munster, Germany) was used for image acquisition.

Scanning Electron Microscopy (SEM)

The same incubation procedures as for the TEM experiment were performed in the SEM studies. All cells were fixed with McDowell's fixative at 4° C., overnight. For post-fixation, 1% osmium tetroxide was used and dehydration was accomplished with a graded series of ethanol. Hexamethyldisilazane was applied for chemical drying. Specimens were mounted on aluminum stubs and prior to examination sputter coated for 90 s. Samples were analyzed on a JEOL JSM-6300 scanning electron microscope (JEOL, Akaishima, Japan) and image acquisition was carried out via an EDAX Phoenix EDAM III data acquisition module (EDAX Inc., Mahwah, N.J., USA).

Results and Discussion

As a first step towards a shorter peptide, the model antimicrobial peptide (AMP) (14 amino acids) of 1b was replaced with a series of short AMP's consisting of alternating tryptophan and arginine residues (1-6 amino acids), see FIG. 1 and Table 1 below.

TABLE 1

| Peptide | Sequence | #AA | SI-1 |
|---|---|---|---|
| 1b | KLAKLAKKLAKLAK-GG-RRRRRRR (SEQ ID NO: 9) | 23 | 5 |
| 2 | W-GG-RRRRRRR (SEQ ID NO: 10) | 10 | n.d. |
| 3 | RW-GG-RRRRRRR (SEQ ID NO: 11) | 11 | n.d. |
| 4a | WRW-GG-RRRRRRR (SEQ ID NO: 12) | 12 | n.d. |
| 5 | RWRW-GG-RRRRRRR (SEQ ID NO: 13) | 13 | n.d. |
| 6a | WRWRW-GG-RRRRRRR (SEQ ID NO: 14) | 14 | 17 |
| 7 | RWRWRW-GG-RRRRRRR (SEQ ID NO: 15) | 15 | 12 |
| 4b | WR(Tbt)-GG-RRRRRRR (SEQ ID NO: 16) | 12 | 2 |
| 4c | (Tbt)R(Tbt)-GG-RRRRRRR (SEQ ID NO: 17) | 12 | 1 |

A surprisingly large difference in activity ($\Delta IC_{50}=58$ μM) was obtained between peptides 2 (a 10mer) and 4a (a 12mer) suggesting that a minimum level of hydrophobicity and charge is necessary for high activity. Only a minor effect was seen when one or both tryptophans of 4a were replaced with the ultra-hydrophobic Tbt amino acid (→4b and 4c, respectively). The incorporation of a third tryptophan (→6a) also had little effect. A small increase in activity ($\Delta IC_{50}<5$ μM) was seen for 4b and 6a, while in the case of 4c a small and unexpected decrease in activity was observed. It thus appears that there is a lower and upper limit wherein hydrophobicity plays a positive role in activity.

A further increase of charge (see 4a→5 and 6a→7) led only to a minor influence on activity ($\Delta IC_{50} \approx 1$ μM).

During the initial screening process peptide analogues was tested against normal human fibroblasts (SI-1) and the results used to estimate cytotoxicity towards healthy cells surrounding the tumor.

SI-1 values for the five most active peptides from the A20 lymphoma screening were determined. The Tbt-peptides, 4b and 4c, exhibited almost no selectivity at all, while the KLA-peptide, 1b, only had low selectivity. In contrast, both the RW-peptides, 6a and 7, showed high selectivity with SI-1 values higher than 10. Although 6a had a slightly lower activity against A20 it is one amino acid shorter and has a significantly better SI-1 than 7. Thus with our integrated criteria of activity, selectivity and peptide length in mind, 6a was selected for further study.

A steady decrease in activity against both A20 and MRC-5 cells was seen with each arginine being removed, see FIG. 2 and Table 2 below.

TABLE 2

| Peptide | Sequence | #AA | SI-1 |
|---|---|---|---|
| 8 | WRWRW-GG-RRRRRR (SEQ ID NO: 18) | 13 | 21 |
| 9 | WRWRW-GG-RRRRR (SEQ ID NO: 19) | 12 | 23 |
| 10 | WRWRW-GG-RRRR (SEQ ID NO: 20) | 11 | >23 |
| 6b | WWWGGRRRRRRRRR (SEQ ID NO: 21) | 14 | 9 |
| 6c | WRRRGRRWRGRRRW (SEQ ID NO: 22) | 14 | >100 |
| 11 | WRRRRRWRRRRW (SEQ ID NO: 23) | 12 | >73 |

Two analogues where the hydrophobic tryptophans and cationic arginines were clustered (6b) or spread across the peptide (6c) were prepared and tested. As the $10_{50}$ values against A20 cells were not affected significantly by these rearrangements, it appears that a highly structured conformation is not responsible for these peptides' activity. The SI-1 value for 6b was significantly lower than for 6a, whereas a sharp increase in SI-1 was seen for 6c. Though the $IC_{50}$ values remained nearly constant, the selectivity was increased dramatically when number of consecutive arginines was reduced.

The two glycines were removed (→11) resulting in a slight increase in activity and a noticeable, but acceptable, reduction in SI-1. An apparent correlation between the maximum number of consecutive arginines and their SI-1 values exist for these peptides, see Table 3.

TABLE 3

The effect of maximum number of consecutive arginines on activity and selectivity.

| Peptide | Sequence[a] | #Arg[b] | IC50 | SI-1 |
|---|---|---|---|---|
| 6b | WWWG<u>RRRRRRRRR</u> | 9 | 3,5 | 9 |
| 6a | WRWRWGG<u>RRRRRRR</u> | 7 | 4,1 | 17 |

TABLE 3-continued

The effect of maximum number of consecutive arginines on activity and selectivity.

| Peptide | Sequence[a] | #Arg[b] | IC50 | SI-1 |
|---|---|---|---|---|
| 11 | WRRRRRWRRRRW | 5 | 5,5 | >73 |
| 6c | WRRRGRRWRGRRRW | 3 | 6,1 | >100 |

[a]Longest stretch of consecutive arginines is underlined.
[b]Maximum number of arginines found consecutively in the peptide.

6a and 11 were tested against a panel of human lymphoma cell lines, see FIG. 3. Including the murine A20 cell line, used in the preceding screening rounds, a total of eight cell lines were tested. Both peptides showed excellent activity against B- and T-lymphomas. Overall, 6a is more active than 11 against all lymphoma tested. Both peptides exhibited high activity (<10 µM) against the most common types of B-lymphoma, namely diffuse large B cell (SU-DHL-6) and Burkitt's lymphoma (Ramos and Namalawa). When tested against the three T-lymphoma lines both 6a and 11 displayed very high activity with similar $IC_{50}$ values of 4.6 µM.

When tested against red blood cells (RBC's), neither peptide induced significant hemolysis. Only 2.3% hemolysis was seen for 6a at the maximum concentration (309 µM) tested, while 11 at its maximum concentration (320 µM) led only to 1.1% hemolysis.

Mechanism of Action

The mechanism by which 6a and 11 exert their cytotoxic effect was investigated. Changes to mitochondrial membrane potential ($\Delta\psi_m$) as well as changes to the composition and integrity of cell membranes were examined by using well-established flow cytometry assay.

A20 cells were treated with the peptides and the $\Delta\psi_m$ measured at 60, 120, 180 and 240 minutes using TMRE as dye. The results showed that 6a is faster acting than 11, but that after four hours of treatment the effect on $\Delta\psi_m$ was the same for both peptides, see FIG. 4A. Since many cellular events can affect mitochondrial function, the observed decrease in $\Delta\psi_m$ is not necessarily an indication that the mitochondrial membrane had been lysed.

To test for apoptosis and necrosis, the amount of phosphatidylserine (PS) translocated to the outer cell membrane and cell membrane integrity was quantified by dual labeling with AnnexinV-FITC and PI. A20 cells were treated with the peptides for a period of an hour. Although a significant number of the affected cells stained positive for PS, most (≈60%) showed signs of compromised cell membranes, see FIG. 4B. However, it is not possible to deduce from these results whether cell membrane disruption was due to primary or secondary necrosis.

Caspases are enzymes that play essential roles in apoptosis (programmed cell death). To explore whether apoptosis was induced, the treated cells were screened for activation of caspases using fluorescently labeled substrates. Neither initiator nor effector caspases were activated as shown in FIG. 4C.

Next, cells were treated with 6a and the effect investigated using TEM and SEM. Micrographs were taken at different time points and concentrations. No evidence to support classical apoptosis (e.g. membrane blebbing, condensed chromatin, disrupted mitochondria etc.) was seen, thereby confirming the results from the caspase screen. Instead, signs of extensive necrosis were seen with TEM. Moreover, in a significant number of lysed cells intact mitochondria were still visible (FIG. 5F). This further supports the notion that mitochondrial membrane disruption is not the primary cause of cell death.

However, SEM analysis revealed startling images of affected cells with massive amounts of intracellular material extruding from them. These SEM results are markedly different from previous work done by our group with lytic peptides and lymphoma cells (Berge et al., supra).

Peptide 6a and its most promising analogue, 11 was tested against eight different lymphoma cell lines. Both peptides had impressive activity against most of the cell lines tested. Interestingly, 11 exhibited only low activity against other types of cancer (non-lymphoma) cells, see Table 4. Almost no activity was seen for 11 against normal fibroblast cells.

TABLE 4

| $IC_{50}$ values for peptide 11 against other cancer cell lines. | | |
|---|---|---|
| DU-145 | Prostate carcinoma | 69 µM |
| HT-29 | Colon carcinoma | 70 µM |

A possible explanation might be the fact that lymphoid cells are well endowed with microvilli. The increased cell surface area could allow for a higher ratio of interaction between peptides and cells. However, intracellular differences (e.g. metabolic pathways) specific to lymphoid cells cannot be discounted as the basis for the cytotoxicity.

Example 2—In Vivo Study

Material and Methods

Peptides

The two peptides to be tested 6a (WRWRWGGR-RRRRRR-amide, SEQ ID NO:24) and 11 (WRRRRRWR-RRRW-amide, SEQ ID NO:25) were synthesized in-house following standard Fmoc-protocols. All peptides were purified (>95%) using preparative-HPLC, freeze-dried and used as TFA-salts.

Cell Lines

A20, a naturally occurring murine B cell lymphoma of BALB/c mice origin, was grown in RPMI-1640 medium containing 1.5 g/L sodium bicarbonate, 4.5 g/L glucose, 10 mM HEPES, 1.0 mM sodium pyruvate and 50 µM 2-mercaptoethanol. The cell cultures were maintained in a humidified atmosphere of 5% CO2 at 37° C.

Animals

Female BALB/c mice, 6-8 weeks of age, were purchased from Charles River, Germany. All mice were housed in cages in a specific pathogen-free animal facility according to the local and European Ethical Committee guidelines.

Intralesional Treatment of A20 Lymphomas

A20 tumor cells were harvested, washed in RPMI-1640 and inoculated (i.d.) into the left side of the abdomen in BALB/c mice (5×10$^6$ cells in 50 µl RPMI-1640 per mouse). When the tumor size reached 20 mm$^2$ the mice were split into three groups and treated; Group1—nine mice with the vehicle (0.9% NaCl in sterile H$_2$O), Group2a—eight mice where the tumors were treated with peptide 6a, and Group 3a—nine mice where the tumors were treated with peptide 11. Intralesional injections were performed once a day for three consecutive days.

Tumor size was measured three times a week using an electronic caliper and expressed as the area of an ellipse [(maximum dimension/2)×(minimum dimension/2)×3.4. Animals were killed when the tumor exceeded 100 mm$^2$.

Animals were killed also if the tumor had not reached that size but presented ulcerations or the animals developed metastasis.

Secondary Tumor Challenge

Animals with complete regression of A20 tumors after treatment with 6a and 11 were rechallenged with A20 lymphoma cells. The cells ($5\times10^6$) were inoculated (i.d.) on the right side of the abdomen (contralateral to the first tumor site) four weeks after the animals were cured.

Statistical Analysis

Survival curves were compared by the log-rank test. Groups were compared using one-way ANOVA test with Tukey's multiple comparison. Differences were considered significant when P<0.05.

Results

All animals, except one, inoculated with A20 cells developed tumors and within 6-7 days tumor sizes were large enough (ca. 20 mm$^2$) for peptide treatment to commence.

Within 21 days eight of the nine control mice were euthanized due to tumor size. A clear inhibitory effect on tumor growth in all animals from Groups 2a and 3a was seen when compared with the control animals treated with saline.

Complete tumor regression in six out of nine mice treated with 11 and in four out of eight treated with 6a, see FIG. 6. Both of the treatments showed significantly increased survival with no signs of systemic toxic effects (e.g. tumor lysis syndrome), compared to the controls.

The cured mice were subjected to a tumor challenge with viable A20 lymphoma cells four weeks after treatment. The naïve control mice (Group 4) quickly developed tumors and within eighteen days all mice were euthanized.

Ten days after tumor rechallenge, three out of the four mice cured after treatment with 6a (Group 2b), developed tumors. Tumor growth, however, was significantly slower than in the control animals. The tumors in two of the mice receded before going into complete regression. Somewhat surprisingly, the remaining two animals, were initially tumor free, but developed rapidly growing tumors in their rib area one month later, and had to be euthanized. At the end of the study (two months post tumor rechallenge), only one animal remained tumor-free. When this mouse was sacrificed an autopsy was performed in order to inspect internal organs, lymph nodes in the extremities and gut associated lymphoid tissues for any signs of abnormalities. A "pearl like chain" was discovered in the fat of the gut, but it is unclear if this was malignant or normal lymphoid tissue.

Judging by these results it appears that intralesional treatment with 6a treatment induced an immune response against A20 lymphoma cells. However, tumor growth was only inhibited, and with only one of the four mice remaining tumor free, see FIG. 2, the immune response was not strong enough to inhibit tumor growth.

Similar results were initially seen for the mice cured after treatment with 11 (Group 3b). Within 10 days after the tumor rechallenge, five of the six mice developed measurable tumors that receded and went into complete regression. However, unlike Group 2b (with the exception of only one) these animals remained tumor free until the end of the study. Two months post tumor rechallenge, the remaining five (tumor-free) mice, see FIG. 7, were sacrificed and, as with the mouse of Group 2b, an autopsy performed. None of the mice had any signs of abnormality.

Although this was only a pilot study the results could nevertheless be considered as significant and very promising.

Both peptides tested exhibited a primary antitumor effect with the majority of treated mice showing complete tumor regression without causing systemic toxicity. However, a clear difference was seen with the rechallenge study. Although both peptides induced a secondary effect it was only 11 that led to genuine protective immunity.

Example 3—Further In Vitro Study

Peptide of sequence WRWRW-GG-KKKKKKK (SEQ ID NO:26) was tested against A20 cells as described in Example 1. The IC50 value was 13.2 μm; this is active but not as effective as the polyarginine equivalent, peptide 6a.

Example 4—Cardiovascular Toxicity Assessment of EWL-6

Materials and Methods

Test System:

Male Sprague-Dawley (Charles River, Portage, Mich.) rats (320-400 g) were instrumented with DSI (St. Paul, Minn.) telemetry transmitters by CorDynamics.

Test Compound, Vehicle and Formulation:

EWL-6 is a peptide having the sequence WGRRRRRG-WGRRRRGW (SEQ ID NO: 8).

EWL-6 was stored in a freezer set to maintain approximately −20° C. and protected from light. A formulation comprising EWL-6 was prepared at a dose volume of 1 mL/kg/dose in 0.9% sodium chloride for injection, U.S.P., for IV dosing. Doses were filtered through a 0.2 μM PP filter prior to injection.

Test Compound Administration:

Each rat was manually restrained and vehicle or EWL-6 dosed twice-daily intravenously over approximately 1-2 minutes. Daily doses were separated by approximately 4 hours.

Hemodynamic Assessment:

Pulse pressure (FIG. 8) and mean arterial pressure (FIG. 9) were recorded for −1 to 8 hours following the first daily dose via telemetry and reported in 1 minute averages from −1 to 8 hours following the first daily dose.

Results

No noticeable difference in pulse pressure (FIG. 8) or in mean arterial pressure (FIG. 9) was seen after either administration of EWL-6 when compared to control, indicating that no cardiovascular toxicity is associated with the peptides of the invention.

The invention claimed is:

1. A peptide having one of the following sequences: WRWRWGGRRRRRRR (SEQ ID NO: 14), WRRRRRWRRRRW (SEQ ID NO: 23) or WGRRRRRGWGRRRRGW (SEQ ID NO: 8).

2. A pharmaceutical composition comprising the peptide of claim 1 and a pharmaceutically acceptable diluent, carrier or excipient.

3. The peptide of claim 1, wherein WRWRWGGRRRRRRR (SEQ ID NO: 14), WRRRRRWRRRRW (SEQ ID NO: 23) or WGRRRRRGWGRRRRGW (SEQ ID NO: 8) is in the form of a salt, ester or amide.

4. The peptide of claim 3, wherein the peptide is in the form of an amide having the sequence of SEQ ID NO: 25.

5. The peptide of claim 3, wherein the peptide is in the form of an amide having the sequence of SEQ ID NO: 24.

6. A method of treating a tumour or cancer cells, which method comprises administering to a subject in need thereof a pharmaceutically effective amount of the peptide of claim 1 or claim 3 or the pharmaceutical composition of claim 2.

7. The method of claim 6, wherein the tumour or cancer cells are a lymphoma.

* * * * *